United States Patent
Kunze et al.

(10) Patent No.: US 12,352,838 B2
(45) Date of Patent: Jul. 8, 2025

(54) METHOD OF RECONSTRUCTING A DYNAMIC SERIES OF MOTION-COMPENSATED MAGNETIC RESONANCE IMAGES

(71) Applicant: Siemens Healthcare GmbH, Erlangen (DE)

(72) Inventors: Karl-Philipp Kunze, London (GB); Radhouene Neji, London (GB)

(73) Assignee: Siemens Healthineers AG, Forchheim (DE)

( * ) Notice: Subject to any disclaimer, the term of this patent is extended or adjusted under 35 U.S.C. 154(b) by 87 days.

(21) Appl. No.: 17/853,902

(22) Filed: Jun. 29, 2022

(65) Prior Publication Data

US 2023/0010419 A1    Jan. 12, 2023

(30) Foreign Application Priority Data

Jun. 30, 2021  (GB) .................................... 2109424

(51) Int. Cl.
*G01R 33/561* (2006.01)
*A61B 5/055* (2006.01)
(Continued)

(52) U.S. Cl.
CPC .......... *G01R 33/5611* (2013.01); *A61B 5/055* (2013.01); *G01R 33/56308* (2013.01); *G01R 33/56509* (2013.01)

(58) Field of Classification Search
CPC .......... G01R 33/5611; G01R 33/56308; G01R 33/56509; G01R 33/561; G01R 33/4818;
(Continued)

(56) References Cited

U.S. PATENT DOCUMENTS 11,782,115 B2 * 10/2023 Kunze ............. G01R 33/56509
                                                    324/309
2016/0038054 A1 * 2/2016 Benner .................. A61B 5/055
                                                    600/413
(Continued)

FOREIGN PATENT DOCUMENTS

DE   102013206315 A1 * 10/2014 ............. A61B 5/113
WO   WO-2022223440 A1 * 10/2022 ......... G01R 33/4826

OTHER PUBLICATIONS

English translation of DE-102013206315-A1 provided by Espacenet. (Year: 2023).*

(Continued)

*Primary Examiner* — Rishi R Patel
(74) *Attorney, Agent, or Firm* — Lempia Summerfield Katz LLC

(57) ABSTRACT

A Computer-implemented method of reconstructing a dynamic series of motion-compensated magnetic resonance images of a patient is provided. Images of a patient are acquired over time, at least partially in free-breathing, at a first image resolution and on a frame-by-frame basis. Each frame of the k-space data includes a first subset of data points having a first sample density and a second subset of data points having a second sample density. For each frame, a sub-group of the first subset and the second subset of the k-space data is selected, and an image is reconstructed at a second image resolution. The motion between the second image resolution images is estimated in the form of motion fields. The motion information is incorporated into a final reconstruction of a dynamic series of motion-compensated magnetic resonance images of the patient at a third image resolution.

18 Claims, 4 Drawing Sheets

(51) Int. Cl.
*G01R 33/563* (2006.01)
*G01R 33/565* (2006.01)

(58) Field of Classification Search
CPC .............. G01R 33/56366; G01R 33/48; G01R 33/563; G01R 33/4824; A61B 5/055
See application file for complete search history.

(56) References Cited

U.S. PATENT DOCUMENTS

| | | | |
|---|---|---|---|
| 2017/0112449 A1 | 4/2017 | Huang et al. | |
| 2018/0149721 A1* | 5/2018 | Beck | G01R 33/56308 |
| 2020/0405176 A1* | 12/2020 | Nielsen | G01R 33/5676 |
| 2021/0109181 A1* | 4/2021 | Beck | G01R 33/5618 |

OTHER PUBLICATIONS

Ahmed, Abdul Haseeb, et al. "Efficient Reconstruction of Free Breathing Under-Sampled Cardiac Cine MRI." arXiv preprint arXiv:1904.04615 (2019).

Asif, M. Salman, et al. "Motion-adaptive spatio-temporal regularization for accelerated dynamic MRI." Magnetic Resonance in Medicine 70.3 (2013): 800-812.

Breuer, Felix A., et al. "Dynamic autocalibrated parallel imaging using temporal GRAPPA (TGRAPPA)." Magnetic Resonance in Medicine: An Official Journal of the International Society for Magnetic Resonance in Medicine 53.4 (2005): 981-985.

Feng, Li, et al. "XD-GRASP: golden-angle radial MRI with reconstruction of extra motion-state dimensions using compressed sensing." Magnetic resonance in medicine 75.2 (2016): 775-788.

Jung, Hong, et al. "k-t FOCUSS: a general compressed sensing framework for high resolution dynamic MRI." Magnetic Resonance in Medicine: An Official Journal of the International Society for Magnetic Resonance in Medicine 61.1 (2009): 103-116.

Lingala, Sajan Goud, et al. "Accelerated dynamic MRI exploiting sparsity and low-rank structure: kt SLR." IEEE transactions on medical imaging 30.5 (2011): 1042-1054.

Muehlberg, Fabian, et al. "Comparability of compressed sensing-based gradient echo perfusion sequence SPARSE and conventional gradient echo sequence in assessment of myocardial ischemia." European Journal of Radiology 131 (2020): 109213.

Otazo, Ricardo, Emmanuel Candes, and Daniel K. Sodickson. "Low-rank plus sparse matrix decomposition for accelerated dynamic MRI with separation of background and dynamic components." Magnetic resonance in medicine 73.3 (2015): 1125-1136.

* cited by examiner

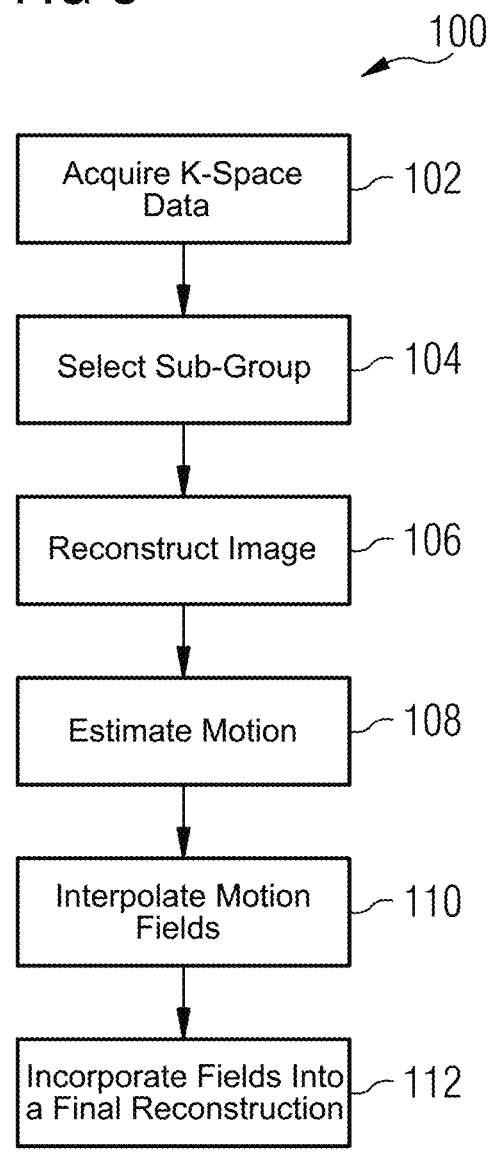

METHOD OF RECONSTRUCTING A DYNAMIC SERIES OF MOTION-COMPENSATED MAGNETIC RESONANCE IMAGES

This application claims the benefit of UK Patent Application No. GB 2109424.8, filed on Jun. 30, 2021, which is hereby incorporated by reference in its entirety.

BACKGROUND

The present embodiments relate to a computer-implemented method of reconstructing a dynamic series of motion-compensated magnetic resonance images of a patient.

Magnetic resonance imaging (MRI) is used frequently in medical applications as a diagnostic and staging tool. A patient is exposed to a static magnetic field Bo and an incident pulsed RF (radio-frequency) signal, which excite the nuclear spin energy transition in hydrogen atoms present in water and fat in the body. Magnetic field gradients are used to localize the resulting magnetization in space, leading to the generation of an image. Varying the parameters of the pulse sequence used to excite the nuclear spin energy transition creates different contrasts between tissues due to the relaxation properties of the hydrogen atoms. Such imaging techniques are used in neurological, cardiovascular, musculoskeletal and gastrointestinal investigations, as well as angiography. Images may or may not be obtained with the use of contrast agents, such as gadolinium, to highlight features of interest.

In cardiovascular imaging, one major issue encountered in the reconstruction of images obtained using MRI is the handling of motion corruption. Typically, MRI acquisition relies on the patient remaining very still, which for scans of limbs or the spine, for example, is likely to be sufficient to provide the acquisition of an uncorrupted image. However, in cardiovascular imaging, motion compensation is a key topic, as cardiac motion and/or respiratory motion may create corruption within the final MRI image, regardless of whether this is a static or a dynamic image. In dynamic MRI imaging, the main challenge arises from the need to capture multiple images of tissue perfusion after injection with a contrast agent, with each image having a small temporal footprint. Typically, this requires a series of very fast (e.g., of the order of 25 ms to 1000 ms) single-shot image acquisitions, which, when combined, span a time window of the order of tens of seconds to several minutes, depending on the organ of interest and/or the characteristics of the contrast agent. While respiratory and/or cardiac motion may be frozen during each individual acquisition, relative motion between acquisitions across the series of single shot images introduces a number of challenges for image analysis and reconstruction. In image reconstruction, it is desirable to use frameworks employing some form of regularization through time in order to use the data redundancy across the dynamic image series. This enables a higher acceleration for individual acquisitions to be achieved, which, in turn, may be used to gain image resolution or improve morphologic coverage. Both resolution and morphologic coverage are key factors in the clinical application of dynamic MRI. In the case of myocardial perfusion imaging, the detection of small perfusion defects is essential; hence the need for a higher spatial resolution, in addition to which the morphological coverage in standard clinical techniques is limited to three slices, which may not be sufficient.

One further issue is that regularization through time does not tend to perform well in the presence of motion. Separating, during reconstruction, the effects of motion, MRI artifacts, and changes in image contrast across a dynamic series MRI due to the inflow of contrast agent is not straightforward. While various models exist that include an explicit motion model in the reconstruction (e.g., in the form of motion fields), obtaining accurate and detailed motion information from the highly undersampled data of each single shot acquisition in the first place remains challenging.

The simplest strategy employed for applications across all organs is the use of breath holding. However, the achievable breath hold varies from patient to patient, and is usually too short to be able to perform perfusion analysis. This is especially true of particularly unwell patients, who may not be able to hold their breath at all. Even optimal breath holding of around twenty to twenty-five seconds does not allow for data analysis using more advanced quantitative methods that require longer windows of kinetic data. In addition, the breath hold is to be timed precisely with the injection of a contrast agent, which poses a significant logistical challenge to clinical workflow and patient communication.

An alternative to breath holding is to utilize free-breathing acquisition with retrospective motion correction. This is where the images forming a dynamic series are aligned after reconstruction with respect to respiratory positions. For common reconstructive approaches, such as GeneRalised Autocalibrating Partial Parallel Acquisition (GRAPPA) and SENSitivity Encoding (SENSE), there is no inclusion of temporal regularization across the dynamic series. This limits the use of such techniques to low acceleration factors and consequently low spatial resolution and morphological coverage.

While a number of reconstruction techniques employing temporal regularization have been proposed, these often rely on specific assumptions regarding the nature of the underlying respiratory and/or cardiac motion (e.g., assuming an inherent periodicity and therefore a sparsity in some domain of MRI encoding). While most physiological motion is in general periodic, this is not necessarily the case in patients exhibiting intermittent deep breathing or cardiac arrythmias. This leads to very inhomogeneous respiratory and/or cardiac motion. For dynamic MRI, other approaches exist that make similar assumptions with regards to the separability of the motion and contrast changes due to the injection of the contrast agent and MRI undersampling. These assumptions are also not generally robust in the light of the irregular motion and perfusion patterns seen in a clinical environment.

Other more recent approaches have been aimed at incorporating an explicit motion model, such as motion fields, that include all of the potentially irregular respiratory and/or cardiac motion into the regularization or data consistency terms of the dynamic data reconstruction. Obtaining the explicit motion information relies on a preliminary reconstruction stage, which is not feasible in the approaches outlined above unless the reconstruction includes some temporal regularization due to the highly undersampled data. Employing any temporal regularization at this stage may, however, greatly reduce the fidelity of the motion states displayed in the preliminary reconstruction, which leads to inaccuracies in the estimated motion and therefore failure to correct for it fully in the final dynamic image reconstruction.

SUMMARY AND DESCRIPTION

The present embodiments aim to address these issues by providing, in a first aspect, a computer-implemented method of reconstructing a dynamic series of motion-compensated magnetic resonance images of a patient. The computer-implemented method includes acquiring, over time, at a first image resolution and on a frame-by-frame basis, k-space data of a dynamic series of magnetic resonance images of a patient over successive respiratory and/or cardiac cycles. Each frame of the k-space data includes a first subset of data points having a first sample density and a second subset of data points having a second sample density. The computer-implemented method also includes selecting, for each frame, a sub-group of the first and second subsets of k-space data and reconstructing an image, at a second image resolution, from these selected sub-groups. The computer-implemented method includes estimating the motion between the second image resolution images in the form of motion fields, and incorporating these motion fields into a final reconstruction of a dynamic series of motion-compensated magnetic resonance images of the patient at a third image resolution.

By employing a dedicated spatio-temporal sampling strategy, the preliminary reconstruction of dynamic data is enabled at a potentially lower resolution without temporal regularization. This enables the display of inter-frame motion in dynamic series of frames with superior fidelity compared to existing approaches.

In one embodiment, the first subset of data points has a greater sample density than the second subset of data points. The first subset of data points may be a region undersampled coherently across the dynamic series, and the second subset of data points may be a region undersampled incoherently across the dynamic series.

In one embodiment, the coherently undersampled region is covering the center of k-space.

In one embodiment, the coherently undersampled region is obtained using a time-interleaved undersampling scheme, and the second subset of data points is obtained using a random or pseudo-random undersampling scheme.

The act of selecting a sub-group of k-space data may include resampling the k-space data to reduce the second image resolution to the minimum resolution at which physiological features of interest are resolvable in a reconstructed image.

The act of reconstructing the individual image frames at a second resolution may include spatial regularization of the individual image frames. The act of reconstructing the individual image frames at a second resolution may be carried out without a temporal regularization constraint.

The final reconstruction of a dynamic motion-compensated image series of the patient at a third resolution may include a temporal regularization constraint across the dynamic series of magnetic resonance images. The final reconstruction of a dynamic motion-compensated image series of the patient at a third resolution may include a spatial regularization of the individual image frames and a temporal regularization constraint across the dynamic series of magnetic resonance images.

The act of reconstructing may be carried out using total-variation (TV) regularization.

The method may further include the acts of registering the reconstructed dynamic images on a frame-by-frame basis to determine motion fields, and interpolating the motion fields to a desired third image resolution for the reconstructed dynamic motion-compensated image.

In one embodiment, the third image resolution is the same as the first image resolution. The second image resolution may be lower than the first image resolution.

In one embodiment, the patient is free-breathing for at least a portion of the time over which the k-space data is obtained.

The size of the coherently undersampled region covering the center of k-space is determined by the minimum resolution at which physiological features of interest are resolvable in a reconstructed image.

The present embodiments also provide, in a second aspect, a data processing apparatus adapted to reconstruct a dynamic series of motion-compensated magnetic resonance images of a patient. The data processing apparatus includes an imaging device adapted to acquire, over time, at a first resolution and on a frame-by-frame basis, k-space data of a dynamic series of magnetic resonance images of a patient over successive respiratory and/or cardiac cycles. Each frame of the k-space data includes a first subset of data points having a first sample density and a second subset of data points having a second sample density. The data processing apparatus also includes a processor adapted to select, for each frame, a sub-group of the first and second subsets of k-space data and reconstruct an image, at a second image resolution, from these selected sub-groups. The processor is further configured to estimate the motion between the second image resolution images in the form of motion fields, and incorporate the motion fields into a final reconstruction of a dynamic series of motion-compensated magnetic resonance images of the patient at a third image resolution.

BRIEF DESCRIPTION OF THE DRAWINGS

The present invention will now be described by way of example only, and with reference to the accompanying drawings, in which:

FIG. 3 is a flow chart illustrating a method in accordance with an embodiment;

DETAILED DESCRIPTION

In order to overcome the issues outlined above, embodiments include a magnetic resonance imaging (MRI) sampling and reconstruction strategy that is specially configured to enable both a robust estimation of explicit motion in the form of motion fields between the frames of a dynamic MRI image acquisition while still maintaining the favorable spatio-temporal properties of the sampled data. This enables an effectively temporally regularized reconstruction of the whole dynamic dataset, including the motion fields, to take place. This may be achieved by considering a computer-implemented method of reconstructing a dynamic series of motion-compensated magnetic resonance images of a patient in four distinct stages: data acquisition; interim image reconstruction; motion field derivation; and incorporation into a final image. First, k-space data of a dynamic series of magnetic resonance images of a patient over successive respiratory and/or cardiac cycles is acquired over time, at a first image resolution and on a frame-by-frame basis. The patient may be free-breathing for at least a portion of the time over which the k-space data is obtained. This may provide that the data is obtained entirely while the patient is free-breathing or partially, where there is some data acquisition during a breath-hold. This may be done in two dimensions using a single phase-encoding dimension of k-space, such as in the examples below. Each frame of the k-space data acquired at a first image resolution includes a first subset of data points having a first sample density and a second subset of data points having a second sample density. The differing sample density is achieved by varying the acquisition data undersampling, where MRI undersampling is the decrease in data, usually in the phase-encoding direction, to increase image acquisition speed, leading to shorter scan times without loss of data quality. Next, for each frame, a sub-group of the first and second subsets of k-space data is selected, and an image is reconstructed at a second image resolution from these selected sub-groups. Third, the motion between the second image resolution images is estimated in the form of motion fields. Finally, the motion information is incorporated into a final reconstruction of a dynamic series of motion-compensated magnetic resonance images of the patient at a third image resolution.

Figure 1A:
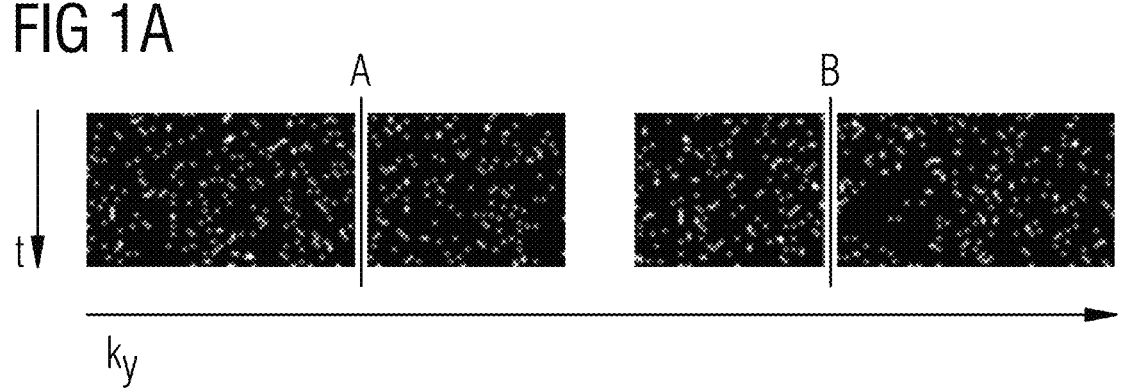
FIGS. 1A-1C are a series of exemplary k-space data patterns illustrating methods of undersampling for forty frames of MRI dynamic data.
Figure 1B:
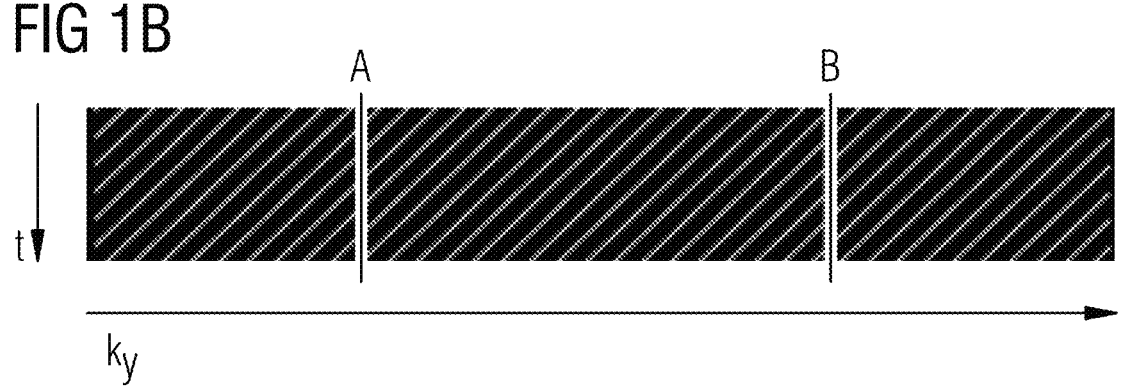
Figure 1C:
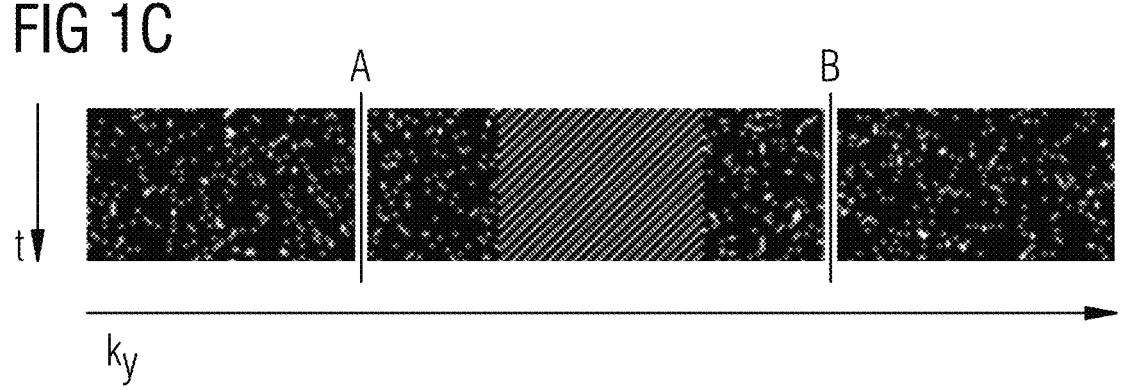

FIG. 1 is a series of exemplary k-space data patterns illustrating methods of undersampling for forty frames of dynamic data. Each image shows a characteristic phase-encoding (ky) sample density based on the method of undersampling used. The acquired first spatial image resolution for each data subset was 1.4 mm$^2$, with a total acceleration factor of 7, where only a fraction of 1/7 of the whole k-space data has been acquired in order to speed up the acquisition. Each of FIGS. 1A, 1B, and 1C represents the phase encoding dimension of k-space data along the x-axis as $k_y$ (omitting the fully sampled read-direction from display), with respect to time t vertically downwards along the y-axis. For each pattern, the horizontal direction therefore shows the acquired phase encodes for a single dynamic frame, with the vertical axis showing the variation in sampling over time. The central region situated between line A and line B contains the phase-encoding data necessary to reconstruct an MRI image series at 2.5 mm$^2$ resolution.

FIG. 1A shows a compressed-sensing type pattern promoting maximum spatio-temporal incoherence having a central fully-sampled region. This is where a random or pseudo-random time-sampling of data points takes place, as shown by the varying data points across the single dimension of k-space shown, evolving over time. FIG. 1B shows a standard, temporally interleaved TGRAPPA pattern, leading to spatially and temporally coherent undersampling. The regular undersampling causes a distinctive diagonal line pattern through time across the single dimension of k-space shown. Finally, FIG. 1C shows a combined pattern having a coherently undersampled central region combined with two regions of incoherently undersampled data. The coherently undersampled central region has a lower degree of temporal sparsity if reconstructed at a reduced resolution (e.g., the region between lines A and B). However, once all of the data is reconstructed, there remains a significant temporal incoherence, as the majority of the data is randomly sampled in a Compressed-Sensing type data pattern.

Figure 2A:
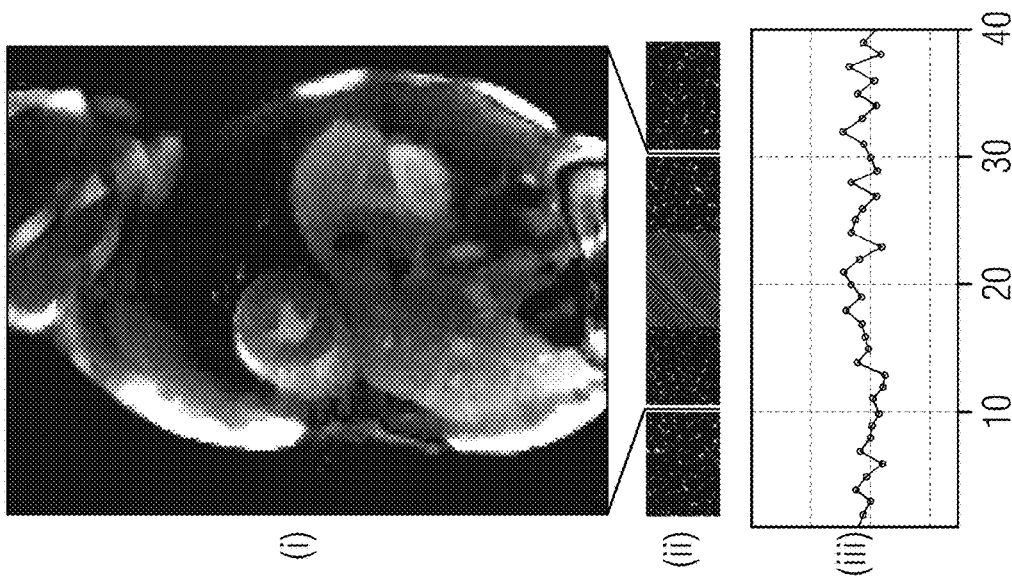
FIGS. 2A-2C illustrate the effect that the undersampling illustrated in FIGS. 1A-1C has on the quality of a reconstructed image.
Figure 2B:
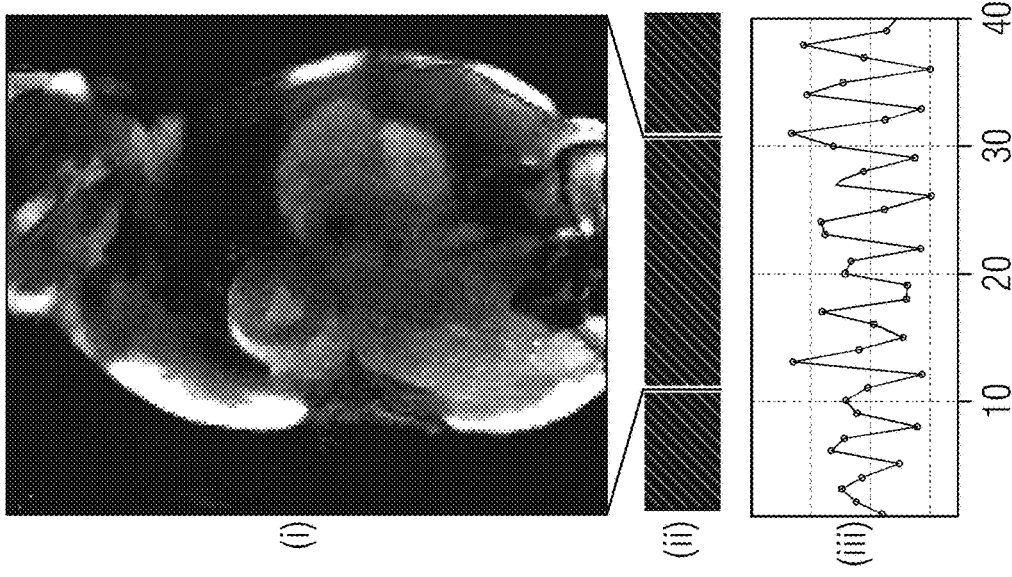
Figure 2C:
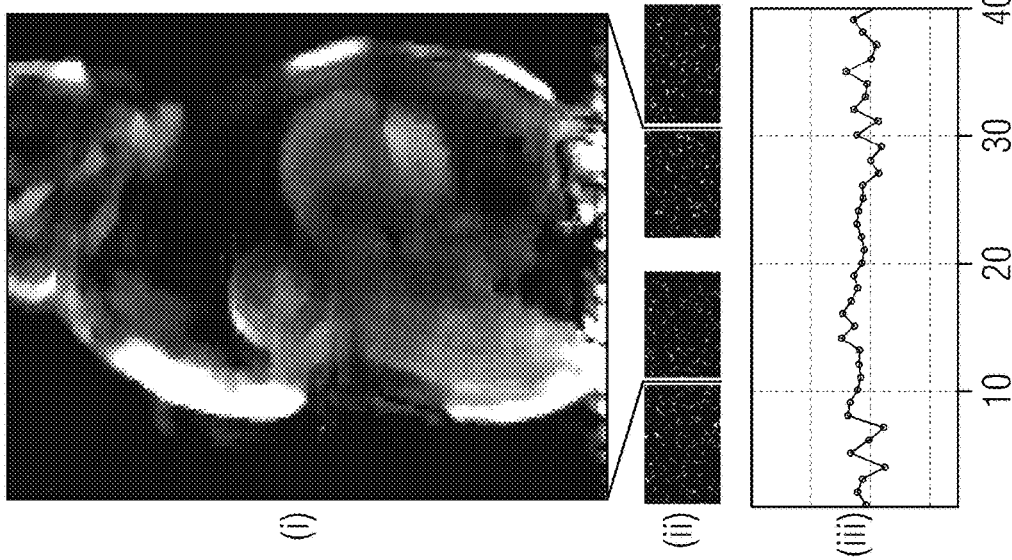
Figure 4A:
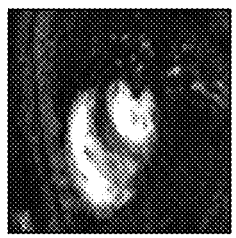
FIG. 4A-4F are a series of comparative images illustrating exemplary single frames from a final reconstruction, both with and without motion correction in accordance with embodiments.
Figure 4B:
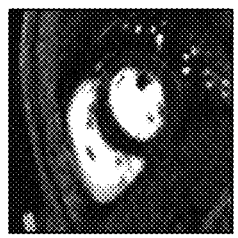
Figure 4C:
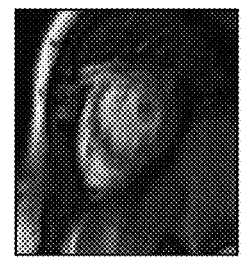
Figure 4D:
Figure 4E:
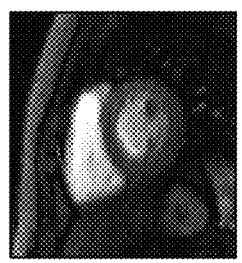
Figure 4F:
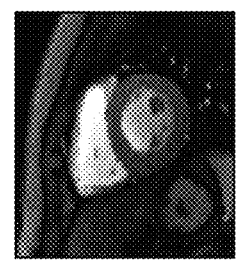

FIG. 2 is an illustration of the effect that the undersampling illustrated in FIG. 1 has on the quality of a reconstructed image. In each of FIGS. 2A, 2B, and 2C, panel (i) shows an example single frame out of the dynamic series of forty frames after preliminary reduced-resolution reconstruction for the estimation of motion fields. The reconstruction employed spatial regularization but no temporal regularization in order to preserve the fidelity of individual motion fields. Panel (iii) illustrates the variation in signal, over time, for the same static region of interest in each of the forty dynamic frames. This is to understand the variation of signal with time unrelated to the effects of motion. In FIG. 2A, the completely incoherent, random sampling of the Compressed-Sensing type pattern shows no significant temporal variation (as shown in panel 2(a)(iii)), but there is incomplete recovery of the anatomical features due to the high undersampling at medium-low spatial frequencies outside the central fully-sampled region. FIG. 2B shows, in panel (i), spatially coherent aliasing in combination with strong temporal signal variation (illustrated by widely varying signals in panel (iii)). This is due to the high undersampling of the k-space center. However, FIG. 2(c) shows that the reconstructed image in panel (i) has no artifacts arising from the moderate (e.g., a factor of 2-3) undersampling of the k-space center, along with little temporal signal variation in panel (iii). Having looked at the effects of combining regions of different data resolutions due to the undersampling techniques chosen, the application of this in the embodiments will now be described in more detail.

FIG. 3 is a flow chart illustrating a method in accordance with an embodiment. The method 100 starts, at act 102, with acquiring, over time, at a first image resolution and on a frame-by-frame basis, k-space data of a dynamic series of magnetic resonance images of a patient over successive respiratory and/or cardiac cycles. The patient may be free-breathing for at least a portion of the time over which the k-space data is obtained. Each frame of the k-space data includes a first subset of data points having a first sample density and a second subset of data points having a second sample density. As in the examples above, the first subset of data points has a greater sample density than the second subset of data points, as the first subset of data points is a region undersampled coherently across the dynamic series, and the second subset of data points is a region undersampled incoherently across the dynamic series. Desirably, the region undersampled coherently is a linearly undersampled region, such as a time-interleaved undersampling scheme, as in Temporal Generalized Autocalibrating Partial Parallel Acquisitions (TGRAPPA), and is located so that the region is centered around the center of the k-space. The second subset of points is temporally incoherent, with a random or pseudo-random sampling scheme, such as the randomly sampled Compressed-Sensing pattern of FIGS. 1 and 2. The second subset of points therefore surrounds this central region on either side of the one-dimensional k-space plot.

Next, at act 104, for each frame, a sub-group of the first and second subsets of k-space data are selected. For all data, this is done using resampling, including, for example, k-space data in read- and phase-encode directions and coil sensitivity maps, to reduce the resolution of the resulting image. The choice of a specific reduced second resolution is balanced between reducing the computing cost (e.g., including time) of carrying out the image reconstruction, reducing the effective undersampling factor of the resampled data, and maintaining sufficient resolution for the physiological features of interest or a respiratory motion amplitude to be resolved. The reduced resolution data now exhibits properties that favor a reconstruction of the individual frames with little or no temporal regularization. Therefore, the second image resolution is lower than the first image resolution. At act 106, an image is reconstructed at a second image resolution, from these selected sub-groups. Spatial regularization of the individual frames may be carried out to reduce any remaining incoherent aliasing from the non-coherently undersampled regions. The act of reconstructing the individual image frames at a second resolution may be carried out without a temporal regularization constraint. Techniques such as total-variation (TV) regularization, which assumes a piece-wise constant image and preserves the edge structure of the image, may be used. The use of such spatial regularization does not corrupt the depiction of motion states in individual frames.

At act 108, the motion between the second image resolution images is estimated in the form of motion fields. For this, each second resolution reconstructed image representing a single time frame is iteratively distorted onto a specific reference frame within the same time series of second resolution images to create vector fields representing the distortion across the dynamic series. At act 110, the motion fields are interpolated to the desired third image resolution for the reconstructed dynamic motion-compensated image.

Finally, at act 112, the motion information is incorporated into a final reconstruction of a dynamic series of motion-compensated magnetic resonance images of the patient at a third image resolution. The reconstruction includes a temporal regularization constraint across the dynamic series of magnetic resonance images. In one embodiment, a spatial regularization of the individual image frames and a temporal regularization constraint across the dynamic series of magnetic resonance images is carried out. This is done by incorporating the motion information either into an MRI encoding operator, or into a regularization constraint across all motion states. Inclusion into an MRI encoding operator (e.g., for a dynamic series off frames) is of the form:

$$E = A_f F S_c U_f$$

where E is the encoding operator, $A_f$ is the sampling pattern (e.g., for all frames f), F is a Fourier operator, $S_c$ represents complex coil sensitivities, and $U_f$ are the motion fields (e.g., for all frames f). The third image resolution may be the same as the first image resolution, such that the final image has the same image resolution as the originally acquired data, or it may have a lower image resolution.

In the examples shown above, the region undersampled coherently is centered around the center of the k-space. The size of the region undersampled coherently in the center of the k-space is determined by the minimum resolution at which physiological features or the motion of interest are resolvable in a reconstructed image. The size of the central region also affects the fidelity of the display of the relevant physiological features and motion in the second resolution reconstructed image, as there is to be a sufficient density of samples in the low- to mid-spatial frequency range. The preferred size of the central region depends on the respective undersampling factors in low- and highly-undersampled regions as well as on the spatial dimensions of the features or motion to be resolved. The examples shown in FIGS. 1 and 2 exhibit a central region of 20% of the first resolution (e.g., 1.4 mm$^2$), leading to a region undersampled coherently encompassing frequency data corresponding to a spatial resolution of up to 7 mm in the phase encoding dimension.

FIG. 4 is a series of comparative images illustrating example single frames both with and without applying the motion fields in accordance with the embodiments. In the reconstruction of the final, third-resolution dynamic series of images (e.g., first and third image resolutions being the same). The data acquisition and processing is summarized in Table 1 below:

TABLE 1 summary of data acquisition and processing for FIG. 4

| Image | Acquisition | Field Strength (T) | Resolution (mm$^2$) | Motion Correction |
|---|---|---|---|---|
| (a) | FLASH* | 3 | 1.4 | No |
| (b) | FLASH | 3 | 1.4 | Yes |
| (c) | TrueFISP** | 1.5 | 1.4 | No |
| (d) | TrueFISP | 1.5 | 1.4 | Yes |
| (e) | FLASH | 3 | 1.3 | No |
| (f) | FLASH | 3 | 1.3 | Yes |

*Fast Low Angle Shot MRI ™
**True Fast Imaging with Steady-State Precession MRI ™, also known as bSSFP (balanced Steady-State Free Precession)

Each image on the right-hand side of FIG. 4 (FIG. 4A, 4C, 4E) is shown without applying the motion fields in the reconstruction. FIG. 4 shows that the overall image quality is poor, with little resolution of areas of interest. For example, in FIG. 4A, the right and left ventricles of the heart are visible, as is the lung vasculature, but it is almost impossible to make any conclusions with regards to perfusion. In contrast, FIG. 4B, where motion-compensated reconstruction in accordance with the present embodiments has been carried out shows the muscle around the left ventricle in much greater detail and sharpness, including even a coronary artery that is not usually seen in perfusion imaging. Similarly with FIG. 4C, the left ventricle of the heart is shown, but little detail of the heart muscle may be made out due to the temporal motion blurring through time, rendering the image undiagnostic for purposes of perfusion analysis. However, in FIG. 4D, the structure of the muscle wall of the left ventricle is clear, along with the heart valves. FIG. 4E is again blurry, with little resolution of either ventricular walls, or the lung vasculature, but in FIG. 4F, all features are displayed in great sharpness.

In the approach outlined above, spatial undersampling artifacts are reduced, along with temporal variations in the signal in the preliminary reconstructions by introducing a linearly undersampled central region into the sampling pattern. A high degree of temporal incoherence for the final reconstruction of data at the full/first resolution is maintained. This is because the central region of relatively low-undersampling is small compared with the remaining region of highly undersampled data in the remainder of k-space; hence, for the final reconstruction, the temporally incoherent, pseudo-random subset represents the majority of the data to be reconstructed, outweighing any effects of the central region of temporally coherent data. Patients may also be imaged while completely free breathing, therefore removing any need for unwell patients to hold their breath and reducing the complexity synchronizing injecting a contrast agent whilst a patient holds their breath.

Figure 5:
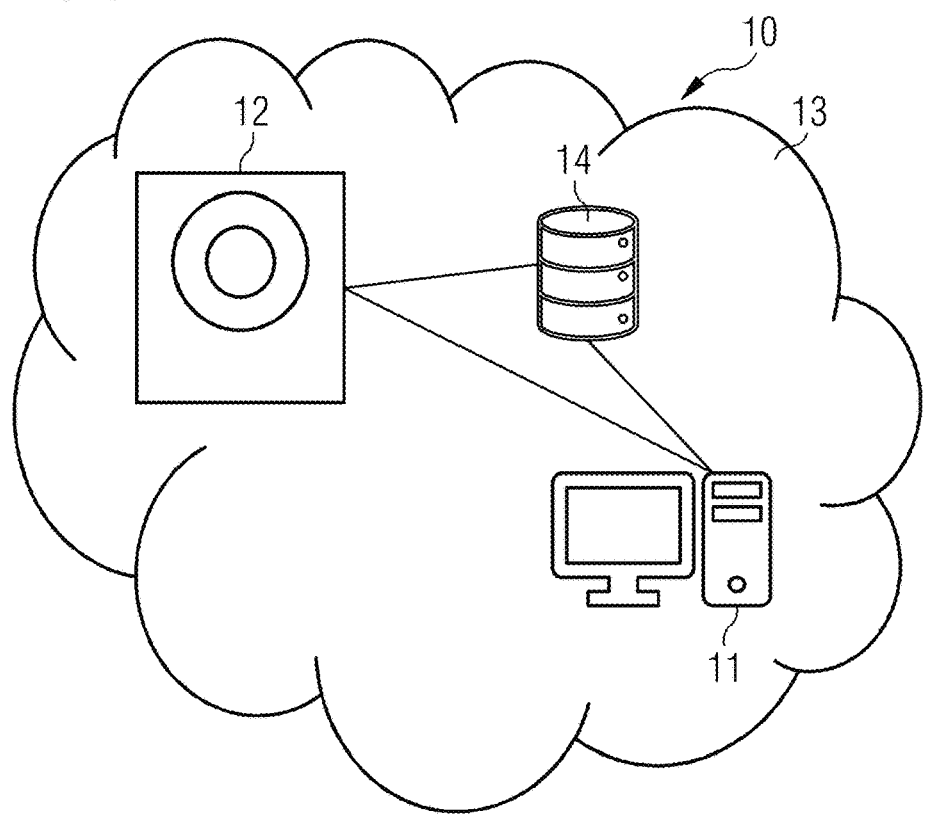
FIG. 5 is a schematic representation of a data processing apparatus adapted to reconstruct a dynamic series of motion-compensated magnetic resonance images of a patient in accordance with embodiments.

FIG. 5 is a schematic representation of a data processing apparatus adapted to reconstruct a dynamic series of motion-compensated magnetic resonance images of a patient in accordance with embodiments. The data processing apparatus 10 includes a processor 11 that is adapted to receive information from an imaging device 12. The imaging device 12 is adapted to acquire, over time, at a first image resolution and on a frame-by-frame basis, k-space data of a dynamic series of magnetic resonance images of a patient over successive respiratory and/or cardiac cycles, where each frame of the k-space data includes a first subset of data points having a first sample density and a second subset of data points having a second sample density. Although the processor 11 may be directly linked to the imaging device 12 by a wired or wireless data connection (e.g., via a communications network 13), data storage 14 is also provided. The data storage 14 may be configured to store raw data directly from the imaging device 12 to be retrieved by the processor 11 when required and is therefore available via the communications network 13 for this purpose. The data storage 14 may also be used to store data during the execution of method acts from the method 100 described above. The processor 11 is therefore adapted to receive or retrieve the k-space data acquired by the imaging device 12. The processor is also adapted to carry out the acts 104 to 112 of the method 100. In addition, a computer program product, including instructions that, when executed on a computer such as the data processing system 10, cause the data processing system 10 to carry out the acts of the method 100.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A computer-implemented method of reconstructing a dynamic series of motion-compensated magnetic resonance images of a patient, the computer-implemented method comprising:
    acquiring, over time, at a first image resolution and on a frame-by-frame basis, k-space data of a dynamic series of magnetic resonance images of the patient over successive respiratory cycles, cardiac cycles, or respiratory cycles and cardiac cycles, wherein each frame of the k-space data comprises a first subset of data points having a first sample density and a second subset of data points having a second sample density;
    selecting, for each frame, a respective sub-group of the first subset of data points and the second subset of data points of the k-space data and reconstructing, for each frame, an image, at a second image resolution, from the selected sub-groups;
    estimating a motion between the second image resolution images in a form of motion fields; and
    incorporating the motion fields into a final reconstruction of the dynamic series of motion-compensated magnetic resonance images of the patient at a third image resolution,
    wherein the first subset of data points is a region undersampled coherently across the dynamic series of magnetic resonance images in a dimension of k-space, and the second subset of data points is a region undersampled incoherently across the dynamic series of magnetic resonance images in the dimension of k-space.

2. The method of claim 1, wherein the first subset of data points has a greater sample density than the second subset of data points.

3. The method of claim 1, wherein the coherently undersampled region is a linearly undersampled region.

4. The method of claim 1, wherein the coherently undersampled region is covering a center of k-space.

5. The method of claim 4, wherein the coherently undersampled region covers the center of k-space across the dynamic series of magnetic resonance images.

6. The method of claim 4, wherein the coherently undersampled region is obtained using a time-interleaved undersampling scheme, and the second subset of data points is obtained using a random or pseudo-random undersampling scheme.

7. The method of claim 4, wherein a size of the coherently undersampled region covering the center of the k-space is determined by a minimum resolution at which physiological features or motion of interest are resolvable in a reconstructed image.

8. The method of claim 1, wherein reconstructing the images at the second image resolution comprises spatial regularization of individual image frames.

9. The method of claim 8, wherein reconstructing the images at the second image resolution is carried out without a temporal regularization constraint.

10. The method of claim 1, wherein the final reconstruction of the dynamic series of motion-compensated magnetic resonance images of the patient at the third image resolution comprises a temporal regularization constraint across the dynamic series of magnetic resonance images.

11. The method of claim 1, wherein the final reconstruction of the dynamic series of motion-compensated magnetic resonance images of the patient at the third image resolution comprises a spatial regularization of the individual image frames and a temporal regularization constraint across the dynamic series of magnetic resonance images.

12. The method of claim 10, wherein the temporal regularization constraint in the reconstructing uses a total-variation regularization.

13. The method of claim 1, further comprising:
    registering the reconstructed images on a frame-by-frame basis to determine motion fields; and
    interpolating the motion fields to a desired resolution for the final reconstruction of the dynamic series of motion-compensated magnetic resonance images.

14. The method of claim 1, wherein the third image resolution is the same as the first image resolution.

15. The method of claim 1, wherein the second image resolution is lower than the first image resolution.

16. The method of claim 15, wherein the second image resolution is chosen as a minimum resolution at which physiological features or a motion of interest is resolvable in a reconstructed image.

17. The method of claim 1, wherein the patient is free-breathing for at least a portion of the time over which the k-space data is obtained.

18. A data processing apparatus adapted to reconstruct a dynamic series of motion-compensated magnetic resonance images of a patient, the data processing apparatus comprising:
    an imaging device configured to acquire, over time, at a first image resolution and on a frame-by-frame basis, k-space data of a dynamic series of magnetic resonance images of a patient over successive respiratory cycles, cardiac cycles, or respiratory cycles and cardiac cycles, wherein each frame of the k-space data comprises a first subset of data points having a first sample density and a second subset of data points having a second sample density; and a processor configured to:
- select, for each frame, a sub-group of the first subset of data points and the second subset of data points of the k-space data;
- reconstruct, for each frame, an image, at a second image resolution, from the selected sub-groups; and
- estimate a motion between the second image resolution images in a form of motion fields and incorporate the motion fields into a final reconstruction of the dynamic series of motion-compensated magnetic resonance images of the patient at a third image resolution, wherein the first subset of data points is a region undersampled coherently across the dynamic series of magnetic resonance images in a dimension of k-space, and the second subset of data points is a region undersampled incoherently across the dynamic series of magnetic resonance images in the dimension of k-space.

* * * * *